(12) United States Patent
Miyanaga et al.

(10) Patent No.: US 6,906,167 B2
(45) Date of Patent: Jun. 14, 2005

(54) PROCESS FOR PRODUCING POLYETHER

(75) Inventors: Seiichi Miyanaga, Wakayama (JP); Hiroshi Kawamukai, Wakayama (JP); Takashi Oda, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/883,827

(22) Filed: Jul. 6, 2004

(65) Prior Publication Data

US 2005/0004344 A1 Jan. 6, 2005

Related U.S. Application Data

(62) Division of application No. 10/082,059, filed on Feb. 26, 2002, now Pat. No. 6,800,723, which is a division of application No. 09/622,592, filed as application No. PCT/JP99/00687 on Feb. 17, 1999, now Pat. No. 6,417,323.

(30) Foreign Application Priority Data

Feb. 20, 1998 (JP) .............................................. 10/38343

(51) Int. Cl.$^7$ .............................................. C08G 65/34
(52) U.S. Cl. ...................... 528/425; 528/402; 528/403; 528/410; 528/411; 528/421
(58) Field of Search ................................ 528/425, 402, 528/403, 410, 411, 421

(56) References Cited

U.S. PATENT DOCUMENTS

| | | | |
|---|---|---|---|
| 4,049,861 | A | 9/1977 | Nozari |
| 4,497,861 | A | 2/1985 | Kistner |
| 4,680,358 | A | 7/1987 | Yu |
| 5,114,619 | A | 5/1992 | Heuvelsland |
| 5,210,325 | A | 5/1993 | Kemp et al. |
| 6,417,323 | B1 | 7/2002 | Miyanaga et al. |

FOREIGN PATENT DOCUMENTS

| | | |
|---|---|---|
| JP | 60-4568 | 1/1985 |
| JP | 62-174229 | 7/1987 |
| JP | 7-109351 | 4/1995 |
| WO | WO 96/19519 | 6/1996 |
| WO | WO 98/15598 | 4/1998 |

OTHER PUBLICATIONS

Y. Zhang et al, Inorganica Chimita Acta, 155, 1989, pp. 263–265.
H. Yasuda et al, Macromol. Chem. Phys. 196, 1995, pp. 2417–2441.
J. Wu et al, Polymer Journal, vol. 22, No. 4, pp. 326–330, "Rare Earth Coordination Catalysts for the Polymerization of Alkylene Oxides I. Polymerization of Epichlorohydrin,", 1990.

*Primary Examiner*—Duc Truong
(74) *Attorney, Agent, or Firm*—Oblon, Spivak, McClelland, Maier & Neustadt, P.C.

(57) ABSTRACT

The present invention provides a process for efficiently obtaining polyethers having its high degree of polymerization by easily polymerizing substituted epoxides which could hardly or could not be made so far to provide a high degree of polymerization. That is, a polyether is obtained by a process which comprises ring-opening-polymerizing at least one substituted epoxide, except for propylene oxide and epihalohydrin, in the presence of a rare earth metal compound represented by the formula (I) and a reducing compound:

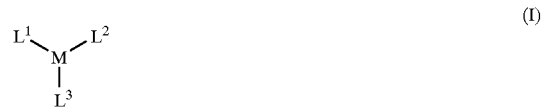

(I)

Wherein M represents a rare earth element selected from Sc, Y and lanthanide, and $L^1$, $L^2$ and $L^3$ are same as or different from each other and each of them represents an oxygen-binding ligand.

12 Claims, 7 Drawing Sheets

PROCESS FOR PRODUCING POLYETHER

This application is a DIV of Ser. No. 10/082,059 filed Feb. 26, 2002 now U.S. Pat. No. 6,800,723, which is a DIV of Ser. No. 09/622,592 filed Sep. 13, 2000 now U.S. Pat. No. 6,417,323; which is a 371 of PCT/JP99/00687 FILED Feb. 17, 1999.

TECHNICAL FIELD

The present invention relates to a process for producing a polyether which has its high degree of polymerization and which is useful in the field of cosmetics and in the field of chemical products and to a novel polyether.

Up to now, in the ring-opening polymerization of a substituted epoxide, a molecular weight of the resultant product has been much decreased in general owing to chain transfer originated from extraction of an atom from the substituent. With respect to propylene oxide and an epihalohydrin, the decrease in the polymerizability is not notably decreased by way of exception. The molecular weight may reach millions by selecting a catalyst. However, with the other substituted epoxide, a polyether having its high degree of polymerization could not be obtained in good yield. This is notably observed in particular in the case of an epoxide having a bulky substituent, such as an epoxide having a long chain alkyl group or a silicone chain as a substituent and an epoxide having a highly electron-attractive fluoroalkyl chain as a substituent. That is, these could not be polymerized in good yield even by using a coordinated anionic catalyst, which is deemed in general to have a high activity as a catalyst for polymerization of epoxide, such as a catalyst comprising organoaluminum-water-acetyl acetone and a catalyst comprising organozinc-water. Further, since an epoxide having a highly reactive hydroxyl group such as glycidol deactivates a coordinated anionic catalyst, it could not be polymerized in high degree without protecting the hydroxyl group.

In recent years, examples of using a composition containing a rare earth metal compound as a catalyst for polymerization of ethylene oxide, propylene oxide or epichlorohydrin are seen in, for example, ① Inorg. Chim. Acta, vol. 155, 263 (1989), ② Polymer J., vol. 22, 326 (1990) and ③ Macromol. Chem. Phys., vol. 196, 2417 (1995). All of these tried to polymerize ethylene oxide, propylene oxide or epichlorohydrin. It is described that polyethyleneoxide having its number average molecular weight of 2,850,000 is obtained in ①, polyepichlorohydrin having its viscosity average molecular weight (deemed to obtain a value being close to a weight average molecular weight) of 790,000 to 1,650,000 in ② and polypropylene oxide having its number average molecular weight of 70,000 to 980,000 (weight average molecular weight of 120,000 to 3,770,000) in ③. However, the degree of polymerization thereof is approximately the same as that of a conventional coordinated anionic catalyst. In consideration of the fact that when a substituted epoxide other than propylene oxide and epihalohydrin (hereinafter referred to as the substituted epoxide) was polymerized using these conventional catalysts, a polyether having its high degree of polymerization could not be obtained. The rare earth metal compound showing approximately the same performance as the conventional catalyst were not expected to be a useful catalyst in order to obtain a polyether having its high degree of polymerization from the substituted epoxide.

DISCLOSURE OF INVENTION

The present invention is aimed to provide a process for efficiently obtaining a polyether having its high degree of polymerization which comprises easily polymerizing a substituted epoxide, other than propylene oxide and epihalohydrin, being hardly or not able to be polymerized in high degree, up to now.

The present invention provides a process for producing a polyether which comprises ring-opening-polymerizing a substituted epoxide, except for propylene oxide and epihalohydrin, in the presence of a rare earth metal compound represented by the formula (I) and a reducing compound and provides a novel polyether obtained thereby:

wherein
M represents a rare earth element selected from Sc, Y and lanthanide, and
$L^1$, $L^2$ and $L^3$ are same as or different from each other and each of them represents an oxygen-binding ligand.

MODE FOR CARRYING OUT THE INVENTION (1) Substituted Epoxide

The substituted epoxide of the present invention means ethylene oxide having a substituent, and examples thereof are as follows.

(1-1) Compounds represented by the formula (II):

wherein
$R^1$ represents a hydrocarbon group which may have a substituent and which has 1 to 50 carbon atoms, represents an acyl group having 1 to 30 carbon atoms, represents an alkyl sulfonyl group having 1 to 30 carbon atoms or an aryl sulfonyl group having 6 to 30 carbon atoms or represents a group represented by $—(AO)_n—R^2$.

Here, $R^2$ represents a hydrocarbon group, a fluoroalkyl group or a fluoroalkenyl group, which may have a substituent and which has 1 to 30 carbon atoms, or a fluoroaryl group, which may have a substituent and which has 6 to 30 carbon atoms, or represents a siloxysilyl group having 1 to 500 silicon atoms. A represents an alkylene group having 2 or 3 carbon atoms. n represents a number selected from 1 to 1,000.

Here, preferable examples of the hydrocarbon groups which may have a substituent with respect of $R^1$ include an alkyl group or alkenyl group having 1 to 42 carbon atoms and an aryl group having 6 to 42 carbon atoms. Examples of the substituent of the hydrocarbon group include a hydroxy group, an alkoxy group (having 1 to 30 carbon atoms), an amino group (a dimethyl amino group, a diethyl amino group or the like), an amide group, a trialkyl ammonium group, a dialkyl ammonium group, an alkyl ammonium group, an ammonium group, an ester group, a carboxyl group, an acyl group (having 1 to 30 carbon atoms), a silyl group, a siloxy group, a nitro group, an aryl sulfonyl group, a cyano group, a phosphonyl group (hereinafter referred to as "the substituent of the present invention"). An alkyl group in this case has 1 to 30 carbon atoms.

A preferable example of the acyl group may be an acyl group having 4 to 22 carbon atoms in total. In this acyl group, a hydrocarbon group may be an alkenyl group.

Further, $R^1$ may be a sulfonyl group having 1 to 30 carbon atoms. A specific example thereof may be a benzenesulfonyl group, a toluenesulfonyl group or a nitrobenzenesulfonyl group.

(1-2) Compounds represented by the formula (III).

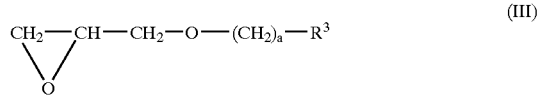

Wherein $R^3$ represents a fluoroalkyl group or fluoroalkenyl group, which may have a substituent and which has 1 to 30 carbon atoms, or a fluoroaryl group which may have a substituent and which has 6 to 30 carbon atoms, and a represents a number selected from 0 to 20.

a is preferably a number selected from 0 to 4. The $R^3$ group is preferably exemplified as trifluoromethyl, pentafluoroethyl, nonafluorobutyl, perfluorohexyl, perfluorooctyl, perfluorododecyl, perfluoro-3-methylbutyl, perfluoro-5-methylhexyl, perfluoro-7-methyloctyl, perfluoro-9-methyldecyl, 1,1-difluoromethyl, 1,1,2,2-tetrafluoroethyl, 4H-octafluorobutyl, 5H-decafluoropentyl, 6H-dodecafluorohexyl, 8H-hexadecafluorooctyl, 10H-icosafluorodecyl, trifluoroethenyl or perfluorophenyl. A preferable example of the substituent of $R^3$ may preferably be "the substituent of the present invention" mentioned above.

In the substituted epoxide (III), a compound having a =0 and the $R^3$ group is a perfluoro group having 1 to 30 carbon atoms is more preferable.

(1-3) Compounds represented by the formula (IV).

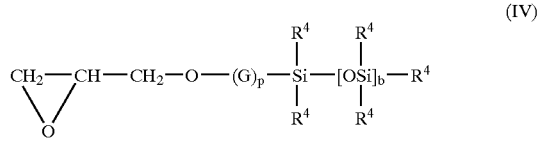

Wherein all of plural $R^4$s are same as or different from each other, and each of plural $R^4$s represents a hydrocarbon group which may have a substituent and which has 1 to 30 carbon atoms or represents a siloxy group having 1 to 200 silicon atoms, G represents an alkylene group, which may have a substituent and which has 1 to 20 carbon atoms, or an arylene group b represents a number selected from 1 to 500 as an average value of plural numbers or represents an integer of 1 to 20 as a single number, and p represents a number selected from 0 and 1.

Here, when the $R^4$ group is a hydrocarbon group which may have a substituent and which has 1 to 30 carbon atoms, examples of the substituent include an ester group, an amide group, an amino group, a hydroxy group and a polyoxyalkylene group.

Preferable examples of the $R^4$ group include a hydrocarbon group having 1 to 10 carbon atoms and a linear or branched siloxy group having 1 to 100 silicon atoms. More preferable examples include a methyl group, a butyl group, a vinyl group and a phenyl group.

When the $R^4$ group is a siloxy group, a group to combine with a silicon atom in the siloxy group may be a methyl group, a butyl group, a vinyl group or a phenyl group.

In the $(G)_p$ group, it may be preferably exemplified that p=0 or p=1 and the G group is a alkylene group such as methylene group, ethylene group and trimethylene group, phenylene group or the like. In view of easiness of the synthesis, the methylene group or the trimethylene group is especially preferable.

In the formula (IV), b represents a chain length of the siloxy group. The chain length may have a distribution or may be a single chain length. Especially, when b is 1 to 20, it is possible that a polyether having a siloxy chain comprising its single chain length is selectively obtained.

Properties of the polyether of the present invention, such as an appearance, an elastic modulus, a solubility in a solvent, vary greatly depending on the value of b. The smaller value of b is, the more remarkably this phenomenon is observed. Further, the smaller the value of b is, the higher a hydrophilic property of the polyether is.

(1-4) Glycidol.

With respect to the substituted epoxide shown in (1-1) to (1-4), two or more of these can be co-polymerized. Further, one or more of these and other epoxy compounds such as ethylene oxide, propylene oxide and/or epichlorohydrin can be co-polymerized. Still further, one or more of these and an anionic-polymerizable monomer can be co-polymerized. Examples of such a monomer include styrene, vinylnaphthalene, 1,3-butadiene, isoprene, 2,3-dimethyl-1, 3-butadiene, 1,3-pentadiene, 1,3-cyclohexadiene, vinyl pyridine, (meth)acrylic acid esters such as methyl methacrylate, episulfides, 4-, 6- or 7-membered lactones, 5- or 6-membered carbonates, lactams and cyclic silicones. More preferable monomer is styrene, 1,3-butadiene, isoprene, methyl methacrylate, β-lactone and hexamethyl cyclotrisiloxane.

(2) Ring-opening polymerization of a substituted epoxide

In the rare earth metal compound represented by the formula (I), which is used in the present invention, examples of M include Sc, Y, La, Ce, Pr, Nd, Pm, Sm, Eu, Gd, Tb, Dy, Ho, Er, Tm, Yb and Lu. Among them, Sc, Y, La, Nd, Sm, Eu, Gd, Dy, Er, Yb or Lu is preferable in view of the polymerization-activity and the economy.

Further, $L^1$, $L^2$ and $L^3$ are oxygen-binding ligands. Examples thereof can include a methoxy group, an ethoxy group, an n-propoxy group, an i-propoxy group, a butoxy group, an allyloxy group, a methoxyethoxy group, a phenoxy group, a 2-methoxypropoxy group, a trifluoroethoxy group, a 2,4-pentanedionato group (acetyl acetonato group), a trifluoropentanedionato group, a hexafluoropentanedionato group, a 6,6,7,7,8,8,8-heptafluoro-2,2-dimethyl-3,5-octanedionato group, a 2,2,6,6-tetramethyl-3,5-heptanedionato group, a thienoyl trifluoroacetonato group, a furoyl trifluoroacetonato group, a benzoyl acetonato group, a benzoyl trifluoroacetonato group, an acetato group, a trifluoroacetato group, a methyl acetoacetato group, an ethyl acetoacetato group, a methyl (trimethyl)acetyl acetato group, a 1,3-diphenyl-1,3-propanedionato group, a methyl sulfonate group, a trifluoromethyl sulfonate group, a dimethyl carbamate group, a diethyl carbamate group, a nitrite group, a hydroxamate group, and an oxygen-binding chelating agent such as an ethylenediamine tetraacetic acid, a diethylene triaminepentaacetic acid, an ethylenediamine tetrakismethylene sulfonic acid, a hydroxy ethylenediamine triacetic acid, nitrilotriacetic acid, and azomethene H. However, the ligand is not limited by them.

Among them, an i-propoxy group, a 2,4-pentanedionato group (acetyl acetonato group), a trifluoropentanedionato group, a hexafluoropentanedionato group, a 2,2,6,6-tetramethyl-3,5-heptanedionato group, an acetato group or a trifluoroacetato group is preferable in view of the polymerization-activity and the economy.

The rare earth metal compound can easily be synthesized by, for example, the reaction of a halide, oxide, hydroxide or nitrate of the rare earth metal with the above-mentioned oxygen-binding ligand or a precursor compound providing the ligand. Each of them may be used after it is previously synthesized and then purified. On the other hand, it may be used in the polymerization system while mixing the rare earth metal compound and the above-mentioned oxygen-binding ligand or the precursor compound providing the ligand.

Further, the rare earth metal compound can be used by being supported on an appropriate carrier if necessary. The type of the carrier is not particularly limited. Any of inorganic oxide carriers, phyllosilicates such as clayey minerals, activated charcoals, metal chlorides, other inorganic carriers and organic carriers may be used. Moreover, the supporting method is not particularly limited, and a publicly known method can be used at the option.

Moreover, the rare earth metal compound may contain an electron-donating ligand such as tetrahydrofuran, diethyl ether, dimethoxy ethane, tetramethyl ethylenediamine, triethyl phosphine.

The amount for use of the rare earth metal compound can be determined, as required, depending on the polymerizability of the said compound, the polymerizable faculty and the amount for use of the substituted epoxide, the desired degree of polymerization and the total amount of the materials which inhibit polymerization and which are present in the reaction system. In the case of the polymerization reaction in a highly purified polymerization system, it is preferably between 0.000001 and 10 equivalents, more preferably between 0.0001 and 1 equivalent, further preferably between 0.0002 and 0.5 equivalent based on the number of moles of the substituted epoxide. When it is at least 0.000001 equivalent, a high polymerization-activity can be obtained. Further, when it is at most 10 equivalents, formation of oligomers (low-molecular polymers) can be inhibited.

The reducing compound used in the present invention may be any compound so long as the compound has a reducibility for reducing the whole or a part of the trivalent rare earth metal compound represented by the formula (I) in order to generate a rare earth metal having quite a high polymerization-activity. Examples thereof for use include (1) an organoaluminum compound such as trimethyl aluminum, triethyl aluminum and triisobutyl aluminum; a two-component catalyst thereof; or a three-component catalyst obtained by adding an alcohol or a chelating compounds thereto; (2) an aluminum trialkoxide; (3) a dialkyl aluminum alkoxide; (4) a dialkyl aluminum hydride; (5) an alkyl aluminum dialkoxide; (6) methylaluminoxane.; (7) an organoaluminum sulfate; (8) a two-component catalyst of an organozinc compound such as dimethyl zinc and diethyl zinc with water; or a three-component catalyst obtained by adding a an alcohol or a chelating compound thereto; (9) a zinc alkoxide; (10) an organolithium compound such as methyl lithium and butyl lithium; and a mixture of one of them and water; and (11) an organomagnesium compound such as dialkyl magnesiums and Grignard reagent; a mixture of one of them and water; and another organic and inorganic compound having its reducibility. Among them, the above-mentioned catalyst (1), (6), (8) or (11) is preferable because it has the appropriate reducibility.

Each of these reducing compounds may be used after it is previously mixed with the rare earth metal compound and then reacted. On the other hand, it may be used in the polymerization-system while being mixed with the rare earth metal. By the way, when it is used after the previous mixing and reaction, it may be retained and aged at an appropriate temperature in order to use it. This aging operation can further increase the polymerization-activity.

The amount for use of the reducing compound can be determined, as required, depending on the reducibility and the type and the amount for use of the rare earth metal compound. When the reducing compound is a compound containing a metal such as aluminum, zinc, lithium and magnesium, the number of moles of the metal for use is preferably between 0.001 and 200 equivalents, more preferably between 0.01 and 100 equivalents and especially preferably between 0.1 and 50 equivalents as compared with the number of moles for use of the rare earth metal. When it is at least 0.001 equivalent, a high polymerization-activity can be obtained. Further, when it is at most 200 equivalents, formation of oligomers (low-molecular polymers) can be inhibited.

When the present invention is being carried out, it is enough that the substituted epoxide is polymerized using the rare earth metal compound represented by the formula (I) and the reducing compound. The temperature for the polymerization is desirable to be in the range of −78 to 220° C., especially −30 to 160° C. The polymerization of the substituted epoxide can be carried out in the absence of a solvent, when the substituted epoxide is in a molten state in the range of the temperature for the polymerization. However, it is usually desirable to carried out the polymerization in an inert solvent.

Examples of such a solvent include hydrocarbons such as benzene, toluene, xylene, ethyl benzene, n-pentane, n-hexane, n-heptane, isooctane and cyclohexane; ethers such as diethyl ether, dipropyl ether, dibutyl ether, tetrahydrofuran and dioxane; and halogenated hydrocarbons such as methylene chloride, chloroform and carbon tetrachloride; as well as N,N-dimethyl sulfoxide and a mixture thereof. Usually, it is good that the solvent selected therefrom for polymerization is used after sufficiently dehydration and deaeration.

Further, the polymerization of the substituted epoxide can also be carried out in a gaseous stream of the substituted epoxide, when the substituted epoxide is in a gaseous state in the range of the temperature for the polymerization.

The polymerization reaction of the present invention is desirably carried out under a condition in which oxygen is excluded. It is desirably carried out under an atmosphere of an inert gas such as nitrogen, helium and argon; under a reduced pressure by deaeration; under a condition introduced with vapor of a solvent by deaeration; or in a gaseous stream of the substituted epoxide. The pressure for polymerization is not particularly limited, and it may be any of normal pressure, reduced pressure or pressurization.

The polymerization reaction of the present invention can be carried out by an optional mixing method. The three members, i.e. the substituted epoxide, the rare earth metal compound and the reducing compound, may be mixed at a time and used. To a system being prepared previously and containing one or two members of these, the remaining two or one member may be added.

When the present invention is being carried out, one or more members thereof can be used as the substituted epoxide. Further, each of these can be used in combination with the other epoxy compound, i.e. ethylene oxide, propylene oxide epichlorohydrin and/or the like. When two or more substituted epoxy compounds are used, these may be mixed at a time and used. These can be introduced into the polymerization system one by one to obtain a block polymer.

Moreover, when the present invention is being carried out, one or more of the substituted epoxides can be used in combination with one or more of anionic-polymerizable monomers other than epoxides. These may be mixed at a time and used or may be introduced into the polymerization system one by one.

(3) Polyether

Examples of the polyether obtained in such a manner are as follows.

(3-1) Polyether represented by the formula (V):

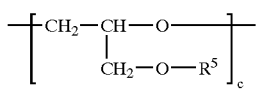
(V)

wherein $R^5$ represents a hydrocarbon group which has 8 to 50 carbon atoms and which may have a substituent, and c represents a number being 150 and more on the average.

Here, the $R^5$ is preferably an alkyl group or alkenyl group having 8 to 42 carbon atoms. When it has a substituent, the substituent is "the substituent of the present invention". The c is preferably between 200 and 1,000,000.

(3-2) Polyether represented by the formula (VI):

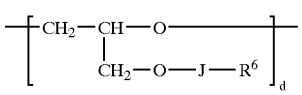
(VI)

wherein $R^6$ represents a fluoroalkyl group having 2 to 30 carbon atoms,

J represents an alkylene group having 1 to 20 carbon atoms, and d represents a number being 5 or more on the average.

Here, the $R^6$ group is preferably a perfluoroalkyl group, or a fluoroalkyl group having 4 to 12 carbon atoms, more preferably a perfluoroalkyl group having 4 to 12 carbon atoms. Further, a polyether wherein at least one terminal group of the $R^6$ groups is a —$CF_2H$ group and the residue obtained by removing the —$CF_2H$ group from the $R^6$ group is a perfluoroalkylene group is also exemplified as a preferable example. For example, it is an ωH-perfluoroalkyl group having a hydrogen atom in its terminal.

The J is preferably an alkylene group having 1 to 5 carbon atoms, more preferably methylene group, ethylene group or trimethylene group. The d is preferably between 20 and 2,000,000, more preferably between 100 and 1,000,000.

(3-3) Polyether represented by the formula (VII):

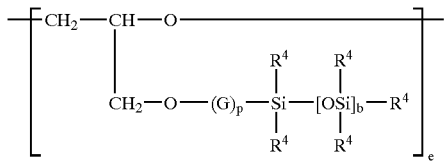
(VII)

wherein $R^4$, G, b and p represent the mean as defined in the formula (IV) in the (1-3) term, and e represents a number being 5 or more on the average.

Here, preferable examples of the $R^4$, G, b and p include those described in the formula (IV) in the (1-3) term.

The e is preferably between 10 and 1,000,000.

(3-4) Polyether represented by the formula (VIII):

(VIII)

wherein

X represents

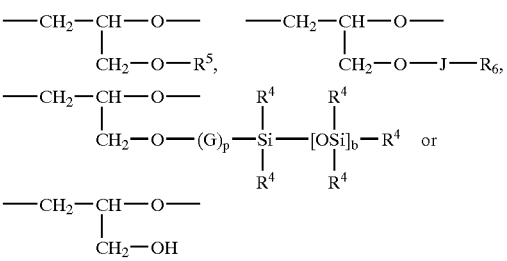

in which $R^5$ represents the mean as defined in the formula (V) in the (3-1) term, $R^6$ and J represent the mean as defined in the formula (VI) in the (3-2) term, and $R^4$, G, b and p represent the mean as defined in the formula (IV) in the (1-3) term, Y represents:

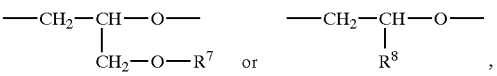

represents a group represented by X (provided that the case in which X and Y are same as each other is excluded), or represents a group originated from an anionic-polymerizable monomer other than the substituted epoxide, in which case Y may be plural types, in which $R^7$ represents a hydrocarbon group having 1 to 7 carbon atoms or represents a trialkyl (an alkyl group has 1 to 4 carbon atoms) silyl group, $R^8$ represents a hydrogen atom or represents a hydrocarbon group or halogen-substituted hydrocarbon group having 1 to 22 carbon atoms, f represents a number being 150 or more when X is

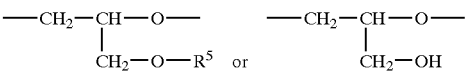

or represents a number being 5 or more when X is the other group, and g represents a number being 5 or more.

Here, the group originated from the anionic-polymerizable monomer refers to a group originated from an anionic-polymerizable monomer being copolymerizable with the substituted epoxide in any of the (1-1) to (1-4) term of the $1^{st}$ term.

The copolymer represented by the formula (VIII) is a system comprising two- or more- component. In the formula (VIII), X and Y may be a random type or may be a block type.

The f is preferably between 150 and 1,000,000 and the g is preferably between 10 and 1,000,000.

EXAMPLES

Figure 1:
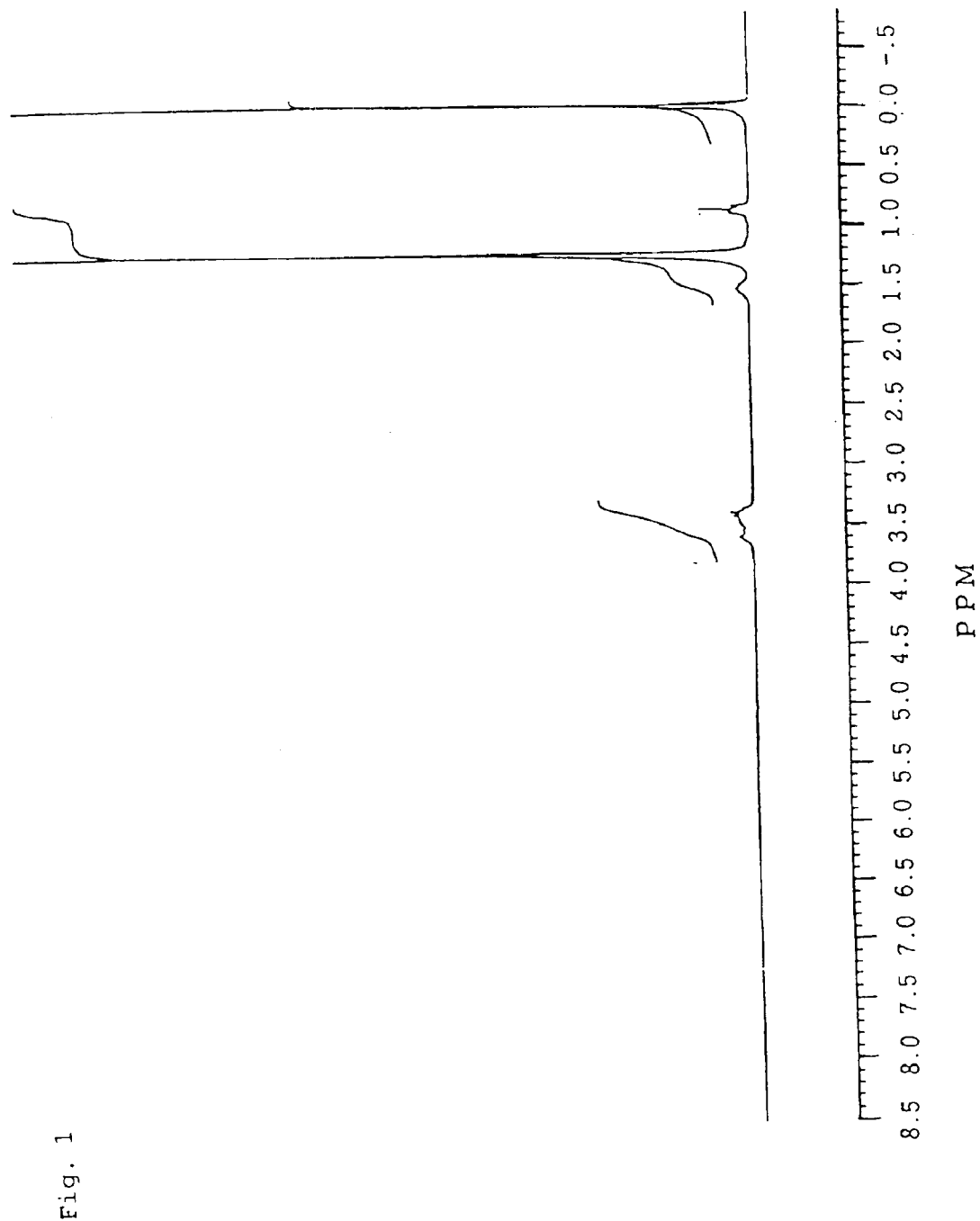
FIG. 1 is an NMR chart of a stearyl glycidyl ether polymer.

The preparation of a catalyst and the operation for polymerization were carried out under an atmosphere of dry nitrogen. Each of various solvents was dried, then distilled and deaerated, therefore it was used. Commercially available and highly pure products of the rare earth metal compound and the other inorganic compound were used as they were. Commercially available products of methylaluminoxane (hereinafter abbreviated as MAO), a solution (a solution used here is a toluene solution and its concentration of aluminum is 10.2% by weight) and diethyl zinc were used as they were.

Preparation Example 1 of Catalyst 0.9296 g of samarium triisopropoxide was basis-weighed, and 23.83 mL of benzene were added thereto. The resultant mixture was stirred. 5.06 mL (6 equivalents) of the MAO solution were added dropwise at room temperature while being stirred to prepare Catalyst A (Sm/Al (molar ratio)=1/6).

Preparation Example 2 of Catalyst 0.5192 g of samarium tris(tetramethyl heptanedionate) was basis-weighed, and 7.20 mL of toluene were added thereto. The resultant mixture was stirred while being heated. After the mixture was left to cool down to room temperature, 0.22 mL (1 equivalent) of the MAO solution was added dropwise while being stirred to prepare Catalyst B (Sm/Al (molar ratio)=1/1).

Preparation Example 3 of Catalyst 0.3181 g of yttrium tris(tetramethyl heptanedionate) was basis-weighed, and 4.96 mL of toluene were added thereto. The resultant mixture was stirred while being heated. After the mixture was left to cool down to room temparature, 0.14 mL (1 equivalent) of the MAO solution was added dropwise while being stirred to prepare Catalyst C (Y/Al (molar ratio)=1/1).

Preparation Example 4 of Catalyst 0.3096 g of samarium tris(trifluoroacetate) was basis-weighed, and 9.70 mL of toluene was added thereto. The resultant mixture was stirred while being heated. After the mixture was left to cool down to room temperature, 0.30 mL (1 equivalent) of the MAO solution was added dropwise while being stirred to prepare Catalyst D (Sm/Al (molar ratio)=1/1).

Preparation Example 5 of Catalyst 0.6485 g of benzoyl trifluoroacetone was dissolved in 2 mL of 95% ethanol, and a matter which comprises 0.12 g of sodium hydroxide being dissolved in 2 ml of distilled water was added thereto while being stirred. After 20 minutes, a 50% ethanol solution (3 ml) of 0.4330 g of lanthanum nitrate with 6 hydrate per molecule thereof was added dropwise to the obtained solution being pale yellow. A solid matter obtained after removal of the solvent by distillation was washed with water and was then dried under reduced pressure at 70° C. for 24 hours.

9.11 mL of toluene were added to the above-obtained lanthanum compound and the resultant mixture was stirred. 0.89 mL (3 equivalents) of the MAO solution was added dropwise thereto to prepare Catalyst E (La/Al (molar ratio)=1/3).

Preparation Example 6 of Catalyst 0.7002 g of samatrium tris(tetramethyl heptanedionate) was basis-weighed, and 7.73 mL of toluene were added thereto. The resultant mixture was stirred while being stirred.

0.20 mL of diethyl zinc was dissolved in 2.00 mL of toluene, and 0.073 mL of glycerol was added thereto while being cooled with ice and stirred. The mixture was stirred at room temperature for 30 minutes and then re-cooled with ice. The previous samarium solution was added thereto. This was aged at 60° C. for 1 hour to obtain Catalyst F (Sm/Zn (molar ratio)=1/2).

Synthesis Example 1

1.74 g of tetraammonium tribromide were added to 50.0 g of 2-(perfluorooctyl) ethanol and 20.0 g of epichlorohydrin under a gaseous stream of nitrogen, and the reaction was carried out in 65 ml of hexane at 40° C. for 10 minutes. While the temperature of the resultant solution was kept at 45° C. or less, 13 g of an aqueous solution containing 48% of NaOH were added dropwise and the solution was further heat for 5 hours while being stirred. The reaction solution was left to cool down, then washed with deionized water and dried. This was distilled under reduced pressure to obtain 3-(1H,1H,2H,2H-heptadecafluorodecyloxy)-1,2-epoxypropane.

Synthesis Example 2

144.5 mL of a hexane solution (1.556 M) of n-butyl lithium was added to 360 mL of tetrahydrofuran (hereinafter referred to as THF) cooled with ice under an atmosphere of nitrogen, and 25.0 mL of tetramethyl silanol which is dried, then distilled and purified was added dropwise. After the resultant mixture was stirred at room temperature for 20 minutes, a solution of 100 g (2 equivalents) of hexamethyl cyclotrisiloxane dissolved previously in 260 mL of THF was added. The resultant solution was stirred at room temperature for 12 hours. The reaction solution was cooled with ice, and 122.5 mL (5 equivalents) of chlorodimethyl silane were added dropwise. The mixed solution was further stirred at room temperature for 2 hours. After that, the solvent, the excess chlorodimethyl silane and the generated lithium chloride were removed. Just then, silicone hydride was obtained as a colorless liquid. According to the NMR analysis, the average number of silicon atoms contained in one molecule was 8.02.

From the above-obtained silicone hydride and an excess amount of allyl glycidyl ether, Silicone Epoxide (1) having a dimethyl silicone chain was obtained by a hydrosilylation reaction. This is provided with G=trimethylene, p=1, $R^4$=methyl and b=7.02 in the formula (IV).

Synthesis Example 3

Silicone hydride having the low boiling point was removed at 75° C. and 26.7 Pa from the silicone hydride obtained in the step of Synthesis Example 2. According to the NMR analysis, the average number of silicon atoms contained in one molecule was 8.72.

From the thus-obtained silicone hydride and an excess amount of allyl glycidyl ether, Silicone Epoxide (2) having a dimethyl silicone chain was obtained by a hydrosilylation reaction. This is provided with G=trimethylene, p=1, $R^4$=methyl and b 7.72 in the formula (IV).

Synthesis Example 4

Silicone hydride was obtained in the same manner as in Synthesis Example 2 except that 50 g (1 equivalent) of hexamethyl cyclotrisiloxane was used instead of 100 g (2 equivalent). This was distilled under reduced pressure at 50° C. and 40 Pa to obtain 1H-undecamethyl pentasiloxane.

From this and an excess amount of allyl glycidyl ether, Silicone Epoxide (3) having a dimethyl silicone chain was obtained by a hydrosilylation reaction. This is silicone epoxide of a single composition and is provided with G=trimethylene, p=1, $R^4$=methyl and b=4.00 in the formula (IV).

Example 1

Poly(stearyl glycidyl ether): $R^5$=Stearyl and c=430 in the Formula (V)

3.266 g of stearyl glycidyl ether were charged into a vessel purged with nitrogen, and 5.7 mL of toluene was added to make the ether dissolved. 1.00 mL of Catalyst A was added thereto and then the vessel was closed with the stopper. The polymerization was carried out at 130° C. with stirring.

After 10 hours, the vessel was opened, and the reaction solution was added to 100 mL of acetone containing a small amount of a dilute solution of hydrogen chloride. A precipitated white solid was dried under reduced pressure at 80° C. for 24 hours to obtain a polyether. Yield 85%.

1.00 g of this polyether was dissolved in 3 ml of chloroform, and this was added to 60 ml of acetone containing a small amount of a dilute solution of hydrogen chloride. A precipitated white solid was dried under reduced pressure at 80° C. for 24 hours to obtain a polyether as a white solid.

According to the GPC analysis (130° C., o-dichlorobenzene, molecular weight calculated as polystyrene), the number average molecular weight (Mn) was 140,000 and the weight average molecular weight (Mw) was 1,610,000. For the measurement, 150C model manufactured by Waters was used and one piece of Shodex HT-806M and two pieces of Shodex HT-803 manufactured by Showa Denko K.K. were used as columns. When the measurement was carried out at 130° C. in the following Examples and Comparative Examples, these conditions were employed.

An NMR (chloroform-$d_1$) chart is shown in FIG. 1. For the measurement, AC200P model manufactured by BRUKER was used.

Figure 2:
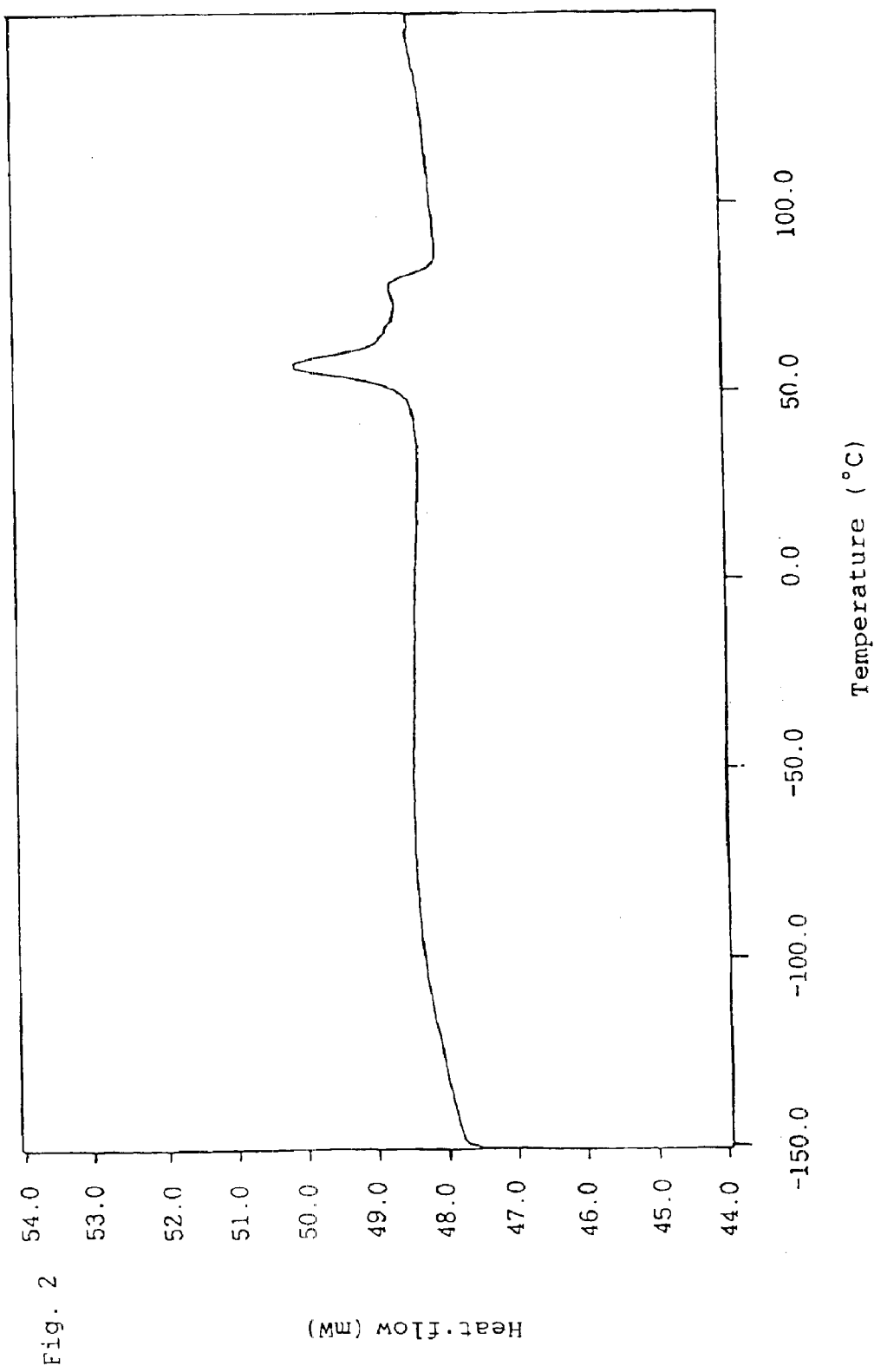
FIG. 2 is a DSC chart of a stearyl glycidyl ether polymer.
Figure 3:
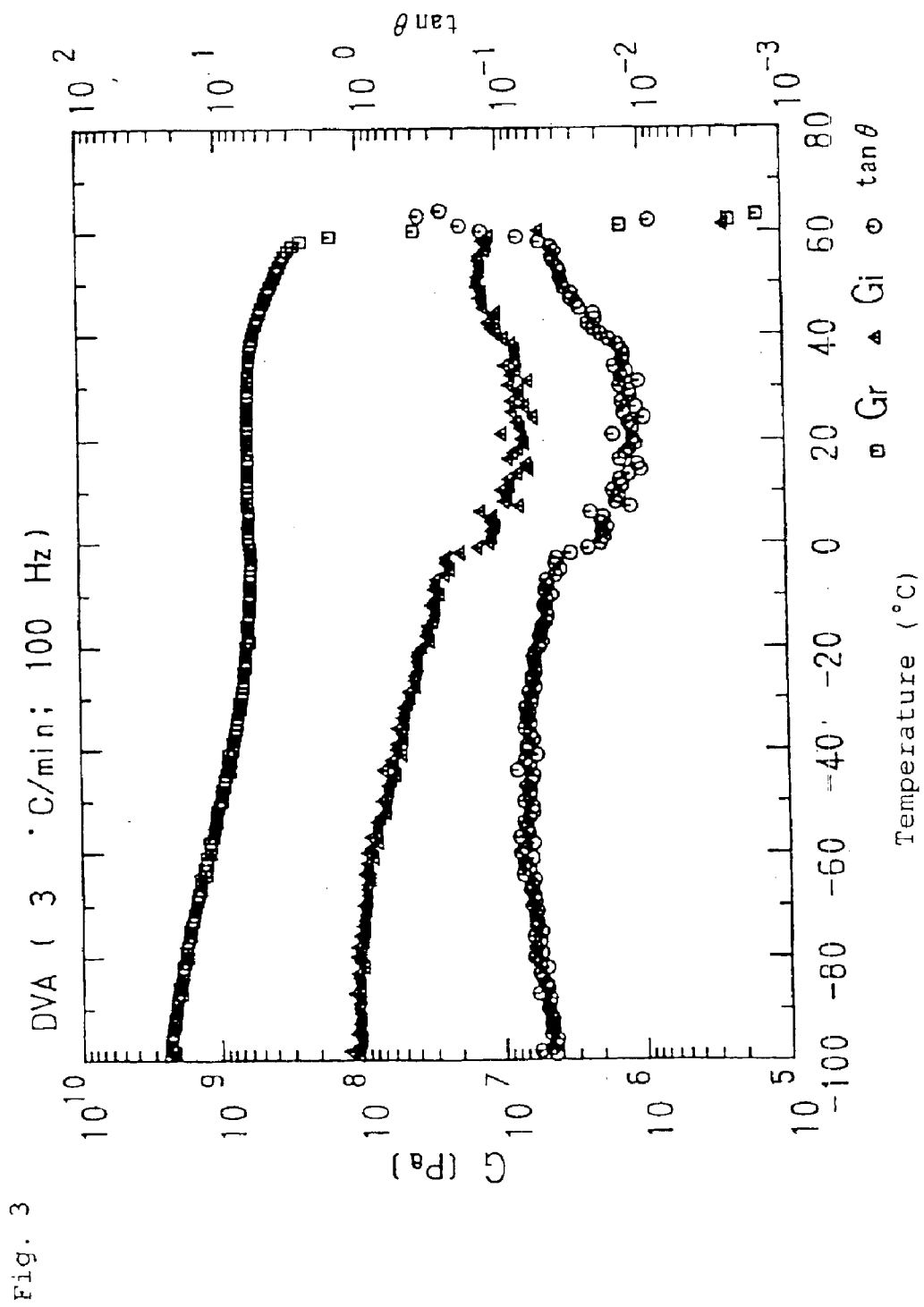
FIG. 3 is a dynamic viscoelasticity chart of a stearyl glycidyl ether polymer.

According to the DSC (FIG. 2) measurement and the dynamic viscoelasticity measurement (FIG. 3), the polyether was a crystalline polymer having melting point of crystalline side chain at 63° C. and being melted uniformly at 84° C. For the DSC measurement, DSC7 manufactured by Perkinelmer was used. For the dynamic viscoelasticity, DVA-225 manufactured by ITK Corp. Ltd. was used.

Example 2

Poly(stearyl glycidyl ether): $R^5$=Stearyl and c=640 in the Formula (V)

A polyether was obtained in the same manner as in Example 1 except that the polymerization was carried out at 100° C. for 24 hours. Yield 84%. White solid.

According to the GPC analysis (130° C.), Mn was 210,000 and Mw was 2,350,000.

Example 3

Poly(stearyl glycidyl ether): $R^5$=Stearyl and c=830 in the Formula (V)

A polyether was obtained in the same manner as in Example 1 except that Catalyst B was used instead of Catalyst A. Yield 99%. White solid.

According to the GPC analysis (130° C.), Mn was 270,000 and Mw was 2,200,000.

Example 4

Poly(lauryl glycidyl ether): $R^5$=Lauryl and c=820 in the Formula (V)

A polyether was obtained in the same manner as in Example 1 except that 2.422 g of lauryl glycidyl ether was used as the substituted epoxide and Catalyst B was used instead of Catalyst A. Yield 100%. White solid. According to the GPC analysis (130° C.), Mn was 200,000 and Mw was 1,900,000.

Example 5

Poly(methyl glycidyl ether): $R^5$=Methyl and c=2,700 in the Formula (V)

0.881 g of methyl glycidyl ether was charged into a vessel purged with nitrogen, and 8.1 mL of benzene were added to make the ether dissolved. 1.00 mL of Catalyst C was added thereto and then the vessel was closed with the stopper. The polymerization was carried out at 120° C. with stirring.

After 6 hours, the vessel was opened, and the reaction solution was added to 100 mL of a solvent which comprises diisopropyl ether mixed with hexane (volume ratio of diisopropyl ether/hexane is 1/1) and which contains a small amount of a dilute solution of hydrogen chloride. A precipitated viscous matter was dried under reduced pressure at 80° C. for 24 hours to obtain a polyether. Yield 93%. Pale yellow and rubbery solid.

According to the GPC analysis (25° C., chloroform, calculated as polystyrene), Mn was 240,000 and Mw was 1,610,000. For the measurement, a pump of CCPD model manufactured by Tosoh Corp. and a differential refractometer of SE-51 model manufactured by Showa Denko K.K. were used; and GMHHR-H, GMHXL, GMPWXL+GMPWXL and AC-G+GMHHR-H+GMHHR-H manufactured by Tosoh Corp. were used as columns. When the measurement was carried out at 25° C. in the following Examples, these conditions were employed.

According to the DSC and the dynamic viscoelasticity measurement, the polyether was found to be amorphous at 25° C.

Example 6

Poly[3-(1H,1H,5H-octafluoropentyloxy)-1,2-epoxypropane]: $R^6$=4H-octafluorobutyl, J=Methylene and d=1,430 in the Formula (VI)

7.00 g of samatrium tris(tetramethyl heptanedionate) were basis-weighed, 450 ml of toluene were added, and the resultant mixture was dissolved by heating. After the solution was left to cool down to room temperature, 17.83 mL of an MAO solution was added dropwise. After 20 minutes, 192.2 g of 3-(1H,1H,5H-octafluoropentyloxy)-1,2-epoxypropane was added, and the vessel was closed with the stopper. The polymerization was carried out at 130° C. for 3 hours with being stirred and then the vessel was opened. The polymerization was terminated with a dilute solution of hydrogen chloride. After the product was cooled to room temperature, a precipitated solid was collected by filtration, washed well with toluene and then dried under reduced pressure. This was dissolved by heating in 4 liters of ethanol and then filtered with a glass filter. The filtrate was charged into deionized water. The precipitated solid was dried under reduced pressure at 80° C. for 24 hours to obtain a colorless rubbery solid polyether. Yield 94%.

According to the GPC analysis (25° C., 50 mmoles/Liter of acetic acid/THF, calculated as polystyrene), Mn was 410,000 and Mw was 1,420,000.

Example 7

Poly[3-(1H,1H,9H-hexadecafluorononyloxy)-1,2-epoxypropane]: $R^6$=8H-hexadecafluorooctyl, J= Methylene and d=250 in the Formula (VI)

A solid polyether having pale yellow was obtained in the same manner as in Example 5 except that 244.1 g of 3-(1H,1H,9H-hexadecafluorononyloxy)-1,2-epoxypropane was used as the substituted epoxide. Yield 93%.

According to the GPC analysis (25° C., 50 mmoles/Liter of acetic acid/THF, calculated as polystyrene), Mn was 120,000 and Mw was 2,180,000.

Example 8

Poly[3-(1H,1H,2H,2H-heptadecafluorodecyloxy)-1, 2-epoxypropane]: in the Formula (VI), $R^6$= perfluorooctyl, J=ethylene and d Being unmeasurable Because it is Insoluble in a Solvent 5.202 g of 3-(1H,1H,2H,2H-heptadecafluorodecyloxy)-1, 2-epoxypropane obtained in Synthesis Example 1 were charged into a vessel purged with nitrogen, and 5.7 mL of toluene were added to make it dissolved. 1.00 mL of Catalyst D was added thereto and then the vessel was closed with stopper. The polymerization was carried out at 130° C. for 3 hours with stirring. The vessel was opened and the polymerization was terminated with a dilute solution of hydrogen chloride. After the product was cooled to room temperature, a precipitated solid was collected by filtration and washed with toluene. This was dried under reduced pressure at 80° C. for 24 hours to obtain a solid polyether being pale yellow. Yield 100%.

Example 9

Polyether Silicone: $R^4$=Methyl, G=Trimethylene, p=1, b=7.02 and e≧28,000 in the Formula (VII)

7.089 g of Silicone Epoxide (1) obtained in Synthesis Example 2 were charged into a vessel purged with nitrogen, and 9.9 mL of toluene were added to make the epoxide dissolved. 3.00 mL of Catalyst E was added thereto and then the vessel was closed with the stopper. The polymerization was carried out at 130° C. with stirring.

After 6 hours, the vessel was opened, and the reaction solution was added to 500 mL of acetone containing a small amount of a dilute solution of hydrogen chloride. A precipitated white gel was dried, then dissolved in chloroform, and charged into acetone containing a small amount of a dilute solution of hydrogen chloride. The generated gel was dried under reduced pressure at 80° C. for 24 hours. Yield 64%. Slightly turbid-white soft solid. It was identified that the polyether was soluble in a solvent such as dichloromethane, chloroform, hexane and hot THF and did not have a crosslinked structure by a side reaction.

Figure 4:
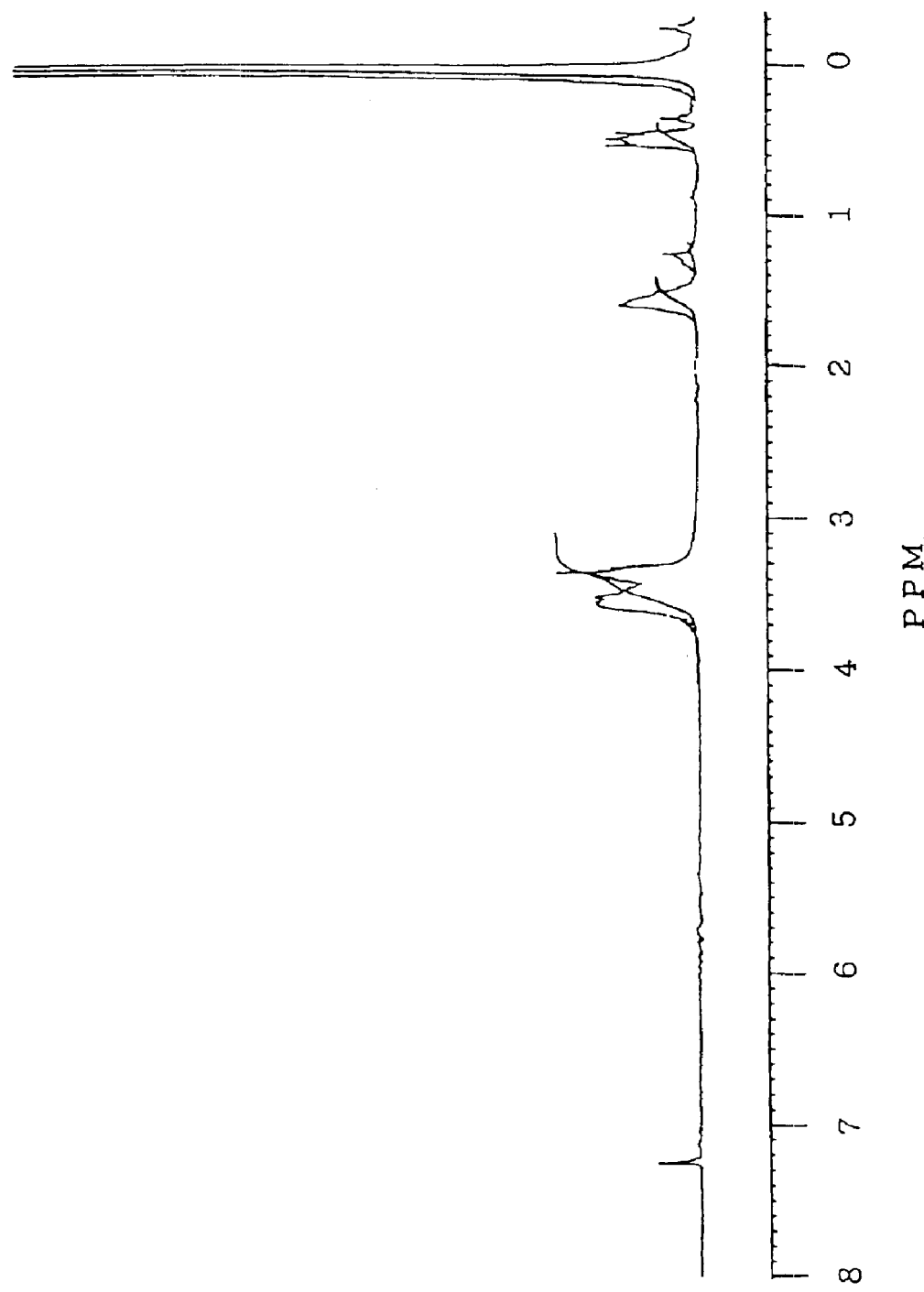
FIG. 4 is a 200 MHz $^1$H NMR chart of a polymer of Silicone Epoxide (1).

According to the 200 MHz $^1$HNMR (chloroform-$d_1$) measurement, it was identified that the polyether had a silicone chain as a side chain (FIG. 4).

Figure 5:
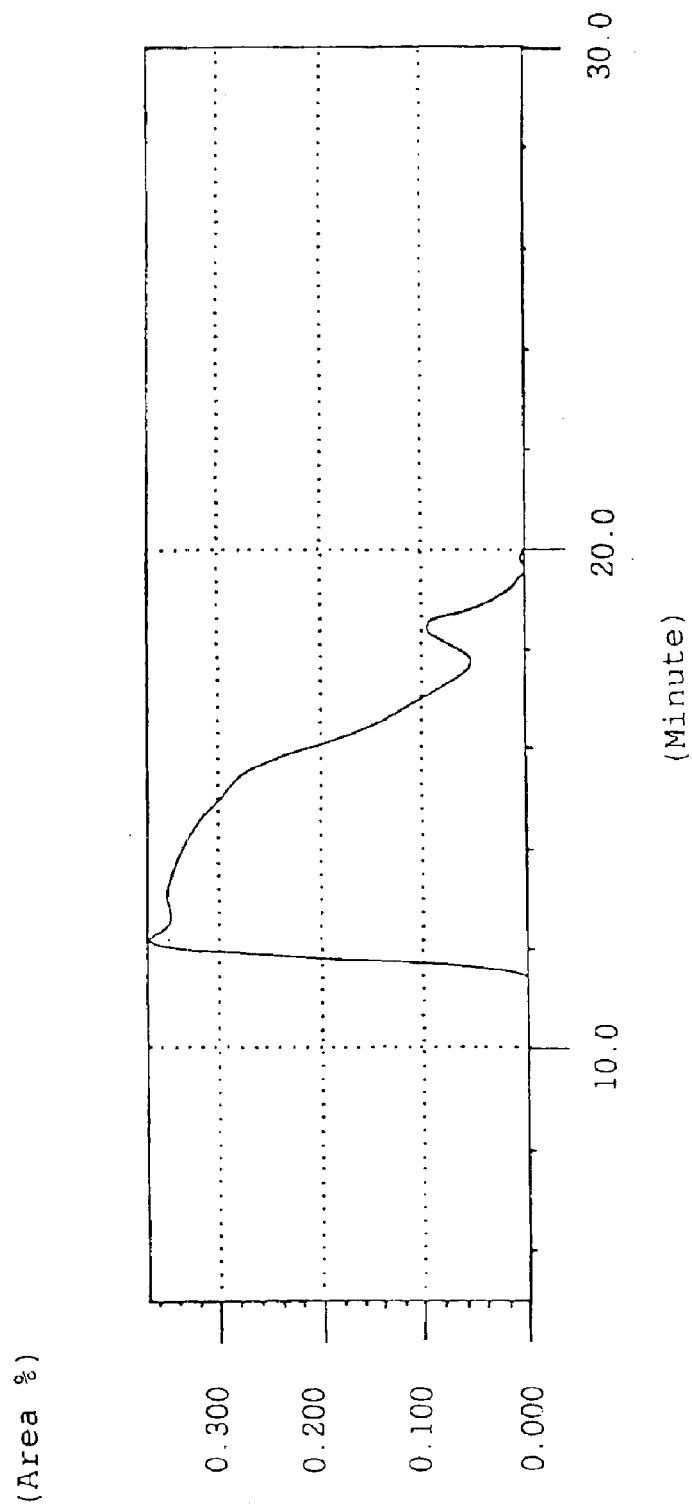
FIG. 5 is a GPC elution curve chart of a polymer of Silicone Epoxide (1).

According to the GPC analysis (25° C., chloroform, calculated as polystyrene) using a set of columns with an exclusion limit of 20,000,000, it was shown that a part of the polyether exceeded this exclusion limit (FIG. 5).

Example 10

Polyether Silicone: $R^4$=Methyl, G=Trimethylene, p=1, b=7.72 and e≧2,600 in the Formula (VII)

The polymerization and the purification were carried out in the same manner as in Example 9 using Catalyst B and 7.608 g of Silicone Epoxide (2) obtained in Synthesis Example 3. Yield 86%. The polyether was a transparent solid having its very soft fluidity. It was identified that the polyether was soluble in a solvent such as dichloromethane, chloroform, hexane and hot THF and did not have a crosslinked structure by a side reaction. According to the NMR (chloroform-$d_1$) measurement, it was identified that the polyether had a silicone chain as a side chain (FIG. 4). Further, according to the GPC analysis (25° C., chloroform, calculated as polystyrene) using a set of columns with an exclusion limit of 20,000,000, it was identified that a part of the polyether exceeded this exclusion limit.

Figure 6:
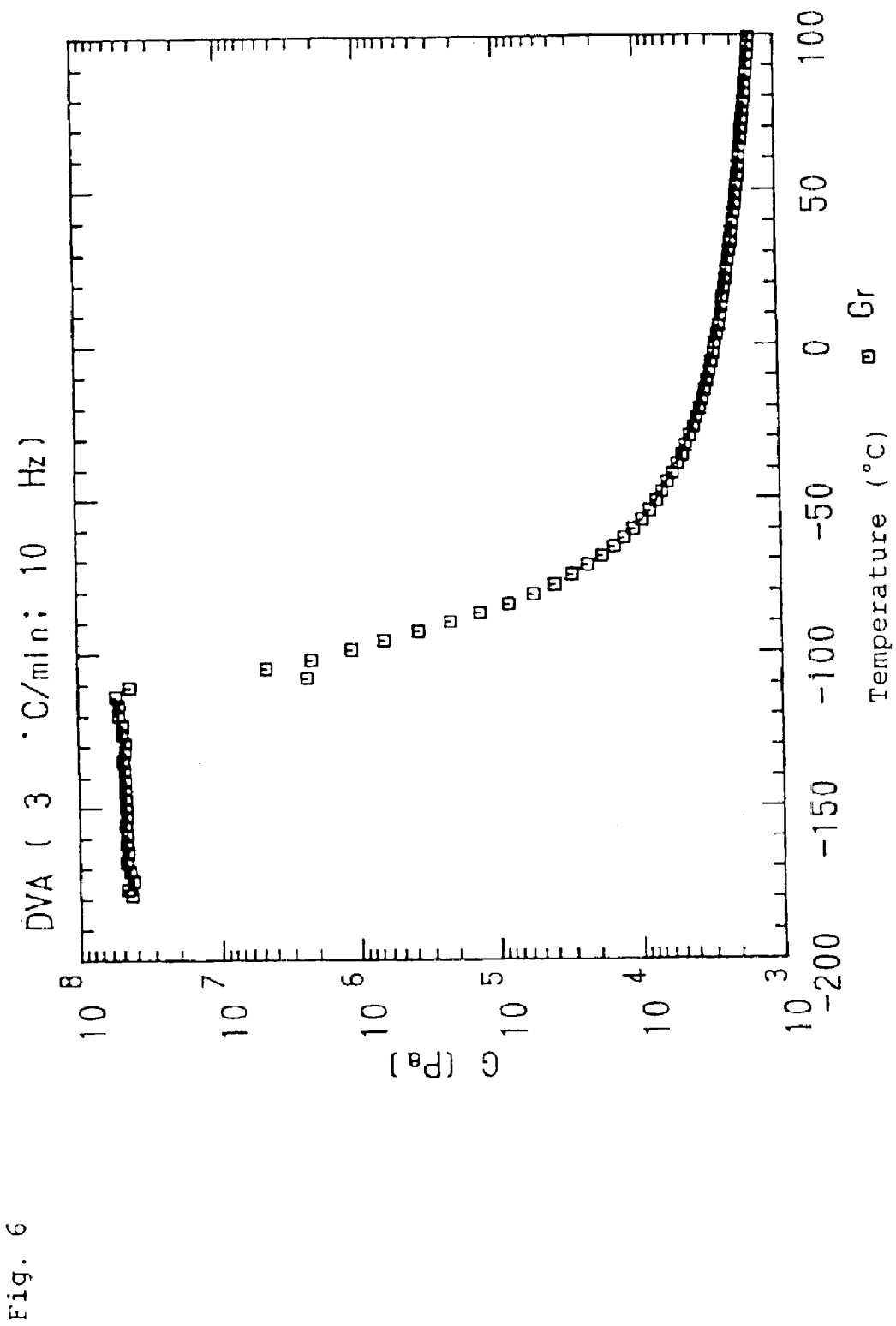
FIG. 6 is a dynamic viscoelasticity chart of a silicone epoxide polymer.

According to the DSC measurement, the polyether was amorphous and the glass transition point was −114.8° C. As the results (FIG. 6) of the dynamic viscoelasticity measurement (−180 to 100° C.) is shown, the elastic modulus at approximately 25° C. was in the order of 103 Pa and it was found to be quite soft. By the way, the elastic modulus at approximately 25° C. of polyethylene glycol having its molecular weight of 5,000,000 is up to $10^8$ Pa and the elastic modulus at approximately 25° C. of polydimethyl silicone [X-21-7784B (Mn=280,000)] manufactured by Shin-Etsu Silicone] is up to $10^5$ Pa.

Example 11

Polyether Silicone: $R^4$=Methyl, G=Trimethylene, p=1 and b=4.00 in the Formula (VII)

The polymerization was carried out for 24 hours in the same manner as in Example 9 using Catalyst F and 4.850 g of Silicone Epoxide (3) obtained in Synthesis Example 4. The vessel was opened, and the reaction solution was added to 500 mL of acetone containing a small amount of a dilute solution of hydrogen chloride. This was filtered with a membrane filter being made of Teflon® and having a pore size of 0.1 μm. The filtrate was concentrated, evaporated to dryness and further dried at 80° C. for 24 hours. Then, a white brittle polymer having its film-like form was obtained. Yield 34%. This polyether was easily powdered. It was insoluble in chloroform and dichloromethane.

According to the DSC measurement, the glass transition point of the polyether was −91.6° C.

Further, according to the dynamic viscoelasticity measurement, the elastic modulus of the polymer at approximately room temperature was $10^5$ Pa.

Example 12

Polyglycidol: the Degree of Polymerization 760

7.408 g of glycidol were charged into a vessel purged with nitrogen and 38 mL of dioxane were added. 0.50 mL of Catalyst B was added thereto and then the polymerization was carried out at 100° C. with stirring.

After 6 hours, a small amount of a dilute solution of hydrogen chloride was added to the reaction solution to terminate the polymerization. Then, it was added to 100 mL of acetone. A white solid was filtered, then washed with isopropyl alcohol, and dried under reduced pressure at 80° C. for 24 hours to obtain polyglycidol. Yield 99%.

5 g of the polyether was dissolved in 50 mL of deionized water, 0.05 g of hinokitiol was added, and the resultant mixture was stirred at 70° C. for 30 minutes. A precipitate was separated by filtration. Then, the obtained aqueous solution was washed with hexane, concentrated, and then re-precipitated and purified with isopropyl alcohol. The precipitate was dried, then re-dissolved in a small amount of water, and freeze-dried to obtain a transparent solid.

According to the GPC analysis (25° C., 0.2 M phosphoric acid/acetonitrile, calculated as polyethylene glycol)., Mn was 56,000 and Mw was 66,000.

Example 13

Poly(stearyl glycidyl ether/octyl glycidyl ether)

$$X = -CH_2-CH-O- \\ \quad\quad\quad | \\ \quad\quad\quad CH_2-O-R^5,$$
($R^5$ = stearyl)
$$Y = -CH_2-CH-O- \\ \quad\quad\quad | \\ \quad\quad\quad CH_2-O-R^5,$$
($R^5$ = octyl)

f=190 and g=280 in the fomula (VIII).

50 mL of Catalyst B, 40.0 g of stearyl glycidyl ether (SGE) and 22.8 g of octyl glycidyl ether (OGE) were added to 210 ml of toluene, and a vessel was closed. The polymerization was carried out at 130° C. for 24 hours with stirring. The reaction solution was added to a large amount of acetone containing a small amount of a dilute solution of hydrogen chloride. A precipitated solid was dried under reduced pressure at 80° C. for 24 hours to obtain a poly (stearyl glycidyl ether/octyl glycidyl ether) copolymer. Pale yellow solid. Yield 75%.

Figure 7:
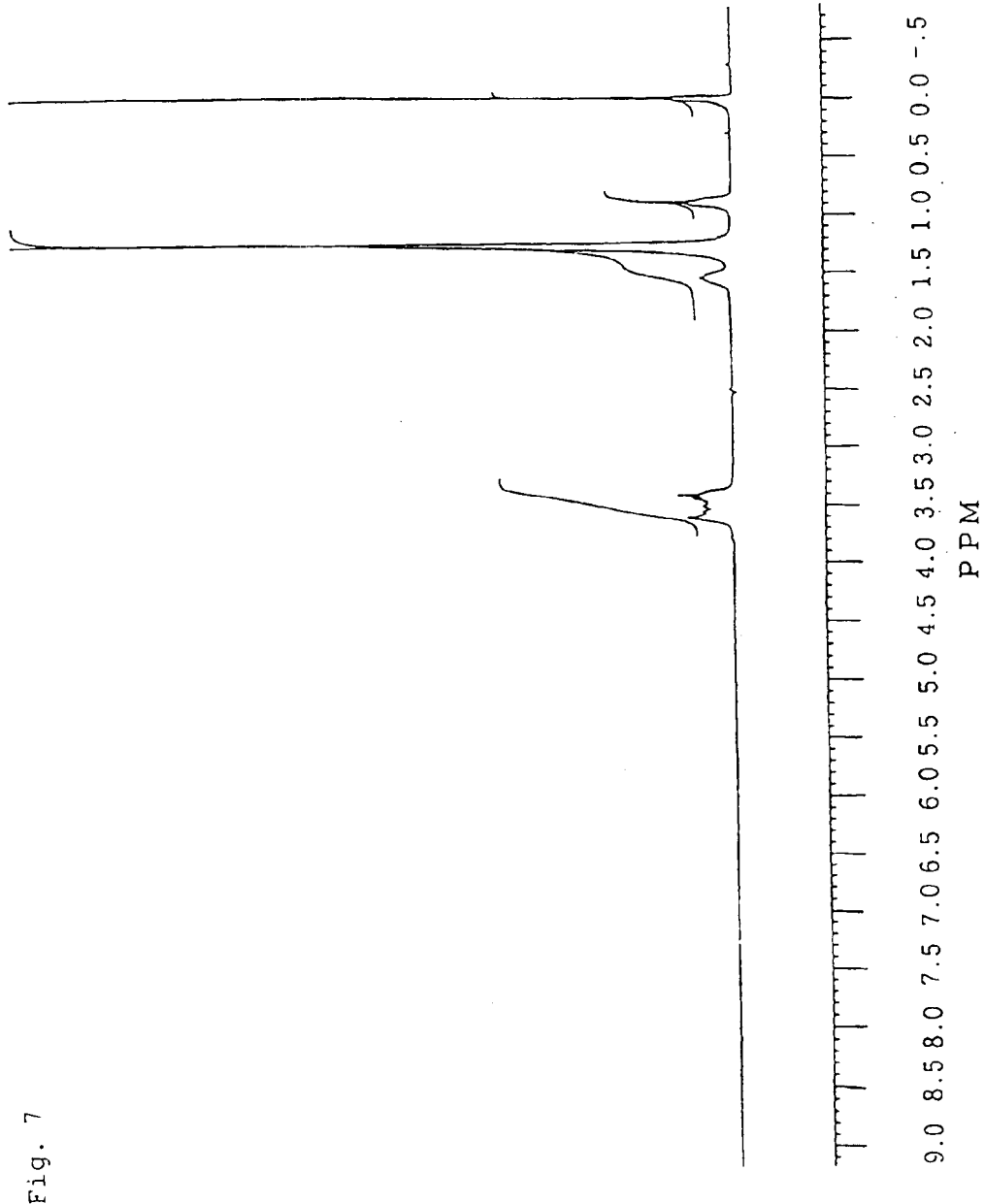
FIG. 7 is an NMR chart of a copolymer of (stearyl glycidyl ether/octyl ether).

According to the NMR (chloroform-$d_1$) analysis, the composition of the polyether was (SGE)/(OGE)=62.3/37.7 (FIG. 7).

According to the DSC measurement, the melting point of the polyether was 32.2° C.

According to the GPC analysis (130° C., o-dichlorobenzene, calculated as polystyrene), Mn was 100,000 and Mw was 1,540,000.

Example 14

Poly(cetyl glycidyl ether/phenyl glycidyl ether)

$$X = -CH_2-CH-O- \\ \quad\quad\quad | \\ \quad\quad\quad CH_2-O-R^5,$$
($R^5$ = cetyl)
$$Y = -CH_2-CH-O- \\ \quad\quad\quad | \\ \quad\quad\quad CH_2-O-R^7,$$
($R^7$ = phenyl)

f=410 and g=240 in the formula (VIII).

111 g of cetyl glycidyl ether (CGE) and 14.0 g of phenyl glycidyl ether (PGE) were co-polymerized in the same manner as in Example 13 to obtain a poly(cetyl glycidyl ether/phenyl glycidyl ether) copolymer. Pale yellow solid. Yield 86%.

According to the NMR (chloroform-$d_1$) analysis, the composition of the polyether was (CGE)/(PGE)=77.2/22.8.

According to the GPC analysis (130° C., o-dichlorobenzene, calculated as polystyrene), Mn was 160,000 and Mw was 1,930,000.

Example 15

Poly(stearyl glycidyl ether/3-(1H,1H,5H-octafluoropentyloxy)-1,2-epoxypropane)

$$X = -CH_2-CH-O- \\ \quad\quad\quad | \\ \quad\quad\quad CH_2-O-R^5,$$
($R^5$ = stearyl)
$$Y = -CH_2-CH-O- \\ \quad\quad\quad | \\ \quad\quad\quad CH_2-O-J-R^6$$
($R^6$ = (1H-octaflurobutyl), J=methylene), f=420 and g=210 in the formula (VIII).

81.6 g of stearyl glycidyl ether (SGE) and 72.0 g of 3-(1H,1H,5H-octafluoropentyloxy)-1,2-epoxypropane (OFPP) were co-polymerized in the same manner as in Example 13. Pale yellow solid. Yield 67%.

According to the NMR (chloroform-$d_1$) analysis, the ratio of the polyether in the composition was (SGE)/(OFPP)= 69.1/30.9.

According to the GPC analysis (130° C., o-dichlorobenzene, calculated as polystyrene), Mn was 200,000 and Mw was 3,600,000.

Example 16

Poly(stearyl glycidyl ether/ethylene oxide): in the General Formula (VIII)

$$X = -CH_2-CH-O- \\ \quad\quad\quad | \\ \quad\quad\quad CH_2-O-R^5,$$
($R^5$ = stearyl)
$$Y = -CH_2-CH-O-, \\ \quad\quad\quad | \\ \quad\quad\quad R^8$$
($R^8$ = hydrogen atom)

and f and g being unmeasurable because it is insoluble in a solvent.

19.4 g of stearyl glycidyl ether (SGE) and 19.4 g of ethylene oxide were co-polymerized in the same manner as in Example 13 except that dioxane was used as a solvent to obtain a colorless solid. Yield 53%.

According to the NMR (chloroform-$d_1$) analysis, the ratio of the polyether in the composition was (SGE)/(ethylene oxide)=3.2/96.8.

Example 17

Poly(stearyl glycidyl ether/methyl methacrylate)

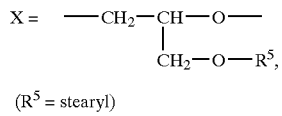

($R^5$ = stearyl)

Y=—$CH_2C(CH_3)$ ($COOCH_3$)—, f=350 and g=44 in the formula (VIII).

50 mL of Catalyst B and 32.6 g of stearyl glycidyl ether (SGE) were added to 210 mL of toluene, and a vessel was closed with the stopper. Then, the polymerization was carried out at 100° C. for 6 hours. The vessel was left to be cool to 40° C., and then opened. 25.0 g of methyl methacrylate was added, and the vessel was closed with the stopper. The polymerization was further carried out at 120° C. for 6 hours. The reaction solution was added to a large amount of acetone containing a small amount of a dilute solution of hydrogen chloride. A precipitated solid was dried under reduced pressure at 80° C. for 24 hours to obtain a poly(stearyl glycidyl ether/methyl methacrylate) copolymer. Colorless solid. Yield 61%.

According to the NMR (chloroform) analyst, the ratio of the polyether in the composition was (SGE)/(methyl methacrylate)=96.3/3.7.

According to the GPC analysis (130° C., o-dichlorobenzene, calculated as polystyrene), Mn was 120,000 and Mw was 980,000.

Comparative Example 1

Stearyl glycidyl ether was polymerized in the same manner as in Example 1 except that a 0.1 M toluene solution of a catalyst obtained by mixing triethyl aluminum, water and acetyl acetone at a molar ratio of triethyl aluminum/water/acetyl acetone being 1/0.5/1 was used instead of Catalyst A. Yield 6%.

According to the GPC analysis (130° C., o-dichlorobenzene, calculated as polystyrene), the polymer had Mn being 40,000 and Mw being 100,000.

Comparative Example 2

Stearyl glycidyl ether was polymerized in the same manner as in Example 1 except that a 0.1 M toluene solution of a catalyst obtained by mixing triethyl zinc and 1-methoxy-2-propanol at a molar ratio of triethyl zinc/1-methoxy-2-propanol being 1/0.5 was used instead of Catalyst A. Yield 87%.

According to the GPC analysis (130° C., o-dichlorobenzene, calculated as polystyrene), the polymer had Mn being 10,000 and Mw being 20,000.

Comparative Example 3

Stearyl glycidyl ether was polymerized in the same manner as in Example 1 except that 0.75 g of cesium hydroxide was used instead of Catalyst A and dimethoxyethane was used instead of toluene. After the operation of re-precipitate, a solid was not obtained at all. Yield 0%.

Comparative Example 4

Silicone Epoxide (1) obtained in Synthesis Example 2 was polymerized in the same manner as Example 12 except that a 0.1 M toluene solution of a catalyst obtained by mixing triethyl aluminum, water and acetyl acetone at molar ratio of triethyl aluminum/water/acetyl acetone being 1/0.5/1 was used instead of Catalyst G. After the operation of re-precipitate, a solid was not obtained at all. Yield 0%.

Comparative Example 5

Glycidol was polymerized in the same manner as Example 18 except that a 0.1 M toluene solution of a catalyst obtained by mixing triethyl aluminum, water and acetyl acetone at molar ratio of triethyl aluminum/water/acetyl acetone being 1/0.5/1 was used instead of Catalyst B. After the operation of re-precipitate, a solid was not obtained at all. Yield 0%.

Test Example (Evaluation of a Gelability of Oils)

A gelability of aliphatic oils was not observed in the stearyl glycidyl ether polymer obtained by using the conventional catalyst for epoxide polymerization (Comparative Examples 1 and 2, number average molecular weight 10,000 to 40,000). Meanwhile, poly(stearyl glycidyl ether) having the high molecular weight in the present invention was found to have its gelability. The polymer in % by weight was added to various oils, and was heated and dissolved at 100° C. for 10 minutes. The resultant mixture was left to be cool to 25° C., and the gelled condition of the oils was visually evaluated. ○: gelled, Δ: quite sticky, x: fluid.

TABLE 1

|  | Liquid paraffin | myristic acid | Soybean oil |
|---|---|---|---|
| Polymer of Example 1 | ○ | ○ | ○ |
| Polymer of Example 2 | ○ | ○ | ○ |
| Polymer of Example 3 | ○ | ○ | ○ |
| Polymer of Example 4 | Δ | Δ | Δ |
| Polymer of Example 5 | x | x | x |
| Polymer of Comparative Example 1 | x | x | x |
| Polymer of Comparative Example 2 | x | x | x |

Industrial Applicability

According to the present invention, a polyether which has its high degree of polymerization and which is useful in the field of cosmetics and in the field of chemical products can be provided easily at good efficiency.

What is claimed is:

1. A polyether represented by the formula (V):

wherein $R^5$ represents a hydrocarbon group which may have a substituent and which has 8 to 50 carbon atoms, and c represents a number being 150 to 1,000,000.

2. A polyether represented by the formula (VI):

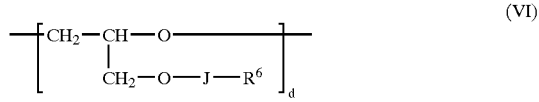

(VI)

wherein $R^6$ represents a fluoroalkyl group having 2 to 30 carbon atoms, J represents an alkylene group having 1 to 20 carbon atoms, and d represents a number being 5 to 2,000,000.

3. The polyether as claimed in claim 2, wherein the $R^6$ group is a perfluoroalkyl group.

4. The polyether as claimed in claim 2, wherein at least one terminal group of the $R^6$ groups is a —$CF_2H$ group and the residue obtained by removing the —$CF_2H$ group from the $R^6$ group is a perfluoroalkylene group.

5. The polyether of claim 1, wherein $R^5$ is an alkyl or alkenyl group.

6. The polyether of claim 1, wherein $R^5$ has 8 to 42 carbon atoms.

7. The polyether of claim 1, wherein c is from 200 to 1,000,000.

8. The polyether of claim 2, wherein $R^6$ is a perfluoroalkyl group having 4 to 12 carbon atoms.

9. The polyether of claim 2, wherein J is an alkylene group having from 1 to 5 carbon atoms.

10. The polyether of claim 2, wherein d is from 20 to 2,000,000.

11. The polyether of claim 2, wherein d is from 100 to 1,000,000.

12. The polyether of claim 1, wherein $R^5$ is an alkyl or alkenyl group having 8 to 50 carbon atoms and c is from 200 to 1,000,000.

* * * * *